(12) United States Patent  
Mernoe

(10) Patent No.: US 8,905,995 B2  
(45) Date of Patent: *Dec. 9, 2014

(54) MEDICINE DISPENSING DEVICE

(75) Inventor: Morten Mernoe, Charlottenlund (DK)

(73) Assignee: Asante Solutions, Inc., Sunnyvale, CA (US)

( * ) Notice: Subject to any disclaimer, the term of this patent is extended or adjusted under 35 U.S.C. 154(b) by 221 days.

This patent is subject to a terminal disclaimer.

(21) Appl. No.: 13/526,967

(22) Filed: Jun. 19, 2012

(65) Prior Publication Data

US 2012/0259310 A1    Oct. 11, 2012

Related U.S. Application Data

(63) Continuation of application No. 13/182,107, filed on Jul. 13, 2011, now Pat. No. 8,226,608, which is a continuation of application No. 12/767,570, filed on Apr. 26, 2010, now Pat. No. 7,998,116, which is a continuation of application No. 10/591,190, filed as application No. PCT/DK2006/000195 on Apr. 6, 2006, now Pat. No. 7,713,238.

(30) Foreign Application Priority Data

Apr. 6, 2005  (DK) ................................. 2005 00483  
Apr. 14, 2005 (DK) ................................. 2005 00542  
Jun. 3, 2005  (DK) ................................. 2005 00817

(51) Int. Cl.
| | |
|---|---|
| *A61M 31/00* | (2006.01) |
| *A61M 5/142* | (2006.01) |
| *A61M 5/145* | (2006.01) |
| *A61M 5/315* | (2006.01) |

(52) U.S. Cl.
CPC . *A61M 5/14276* (2013.01); *A61M 2005/14506* (2013.01); *A61M 2005/31518* (2013.01); *A61M 5/14566* (2013.01); *A61M 5/14244* (2013.01); *A61M 5/1454* (2013.01)  
USPC ........................... 604/500; 604/131; 604/151

(58) Field of Classification Search  
CPC ..................... A61M 5/14244; A61M 5/14276; A61M 5/1454; A61M 5/14566; A61M 2005/14506; A61M 2005/31518  
USPC ......... 604/131, 151-155, 174, 207–211, 500; 128/DIG. 1, DIG. 12  
See application file for complete search history.

(56) References Cited

U.S. PATENT DOCUMENTS

| | | |
|---|---|---|
| 2,605,765 A | 8/1952 | Kollsman |
| 3,886,938 A | 6/1975 | Szabo et al. |

(Continued)

FOREIGN PATENT DOCUMENTS

| | | |
|---|---|---|
| CA | 2543545 | 5/2005 |
| DE | 196 27 619 A | 1/1998 |

(Continued)

OTHER PUBLICATIONS

Accu-Chek Spirit, "Pump Therapy Made for You," Roche, 2006, 6 pages.

(Continued)

*Primary Examiner* — Theodore Stigell  
(74) *Attorney, Agent, or Firm* — Fish & Richardson P.C.

(57) ABSTRACT

Some embodiments of a wearable, disposable medicine dispensing device may include a piston rod that is advanced to dispense medicine from the device. A rotational motor may be coupled to a drive mechanism so as to carry out a certain number of revolutions and thereby displace the piston rod by a desired distance. Such a device can be used in a method of dispensing liquid medicine.

18 Claims, 16 Drawing Sheets

(56) References Cited

U.S. PATENT DOCUMENTS

| | | |
|---|---|---|
| 4,077,405 A | 3/1978 | Haerten et al. |
| 4,231,368 A | 11/1980 | Becker |
| 4,265,241 A | 5/1981 | Portner et al. |
| 4,300,554 A | 11/1981 | Hessberg et al. |
| 4,313,439 A | 2/1982 | Babb et al. |
| 4,373,527 A | 2/1983 | Fischell |
| 4,398,908 A | 8/1983 | Siposs |
| 4,435,173 A | 3/1984 | Siposs et al. |
| 4,443,218 A | 4/1984 | DeCant, Jr. et al. |
| 4,493,704 A | 1/1985 | Beard et al. |
| 4,529,401 A | 7/1985 | Leslie et al. |
| 4,562,751 A | 1/1986 | Nason et al. |
| 4,619,653 A | 10/1986 | Fischell |
| 4,678,408 A | 7/1987 | Nason et al. |
| 4,850,817 A | 7/1989 | Nason et al. |
| 5,045,064 A | 9/1991 | Idriss |
| 5,088,981 A | 2/1992 | Howson et al. |
| 5,190,522 A | 3/1993 | Wojcicki et al. |
| 5,209,230 A | 5/1993 | Swedlow et al. |
| 5,250,027 A | 10/1993 | Lewis et al. |
| 5,261,882 A | 11/1993 | Sealfon et al. |
| 5,314,412 A | 5/1994 | Rex |
| 5,335,994 A | 8/1994 | Weynant Nee Girones |
| 5,338,157 A | 8/1994 | Blomquist |
| 5,342,180 A | 8/1994 | Daoud |
| 5,395,340 A | 3/1995 | Lee |
| 5,411,487 A | 5/1995 | Castagna |
| 5,545,143 A | 8/1996 | Fischell et al. |
| 5,551,850 A | 9/1996 | Williamson et al. |
| 5,569,186 A | 10/1996 | Lord et al. |
| 5,626,566 A | 5/1997 | Petersen et al. |
| 5,637,095 A | 6/1997 | Nason et al. |
| 5,665,065 A | 9/1997 | Colman et al. |
| 5,741,216 A | 4/1998 | Hemmingsen et al. |
| 5,764,034 A | 6/1998 | Bowman et al. |
| 5,772,635 A | 6/1998 | Dastur et al. |
| 5,816,306 A | 10/1998 | Giacomel |
| 5,852,803 A | 12/1998 | Ashby, III et al. |
| 5,919,167 A | 7/1999 | Mulhauser |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,033,377 A | 3/2000 | Rasmussen et al. |
| 6,045,537 A | 4/2000 | Klitmose |
| 6,074,372 A | 6/2000 | Hansen |
| 6,110,149 A | 8/2000 | Klitgaard et al. |
| 6,156,014 A | 12/2000 | Petersen et al. |
| 6,171,276 B1 | 1/2001 | Lippe et al. |
| 6,231,540 B1 | 5/2001 | Smedegaard |
| 6,248,067 B1 | 6/2001 | Causey, III et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,375,638 B2 | 4/2002 | Nason et al. |
| 6,379,339 B1 | 4/2002 | Klitgaard et al. |
| 6,381,496 B1 | 4/2002 | Meadows et al. |
| 6,404,098 B1 | 6/2002 | Kayama et al. |
| 6,427,088 B1 | 7/2002 | Bowman, IV et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |

(56) References Cited

U.S. PATENT DOCUMENTS

| | | |
|---|---|---|
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larson et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,232,423 B2 | 6/2007 | Mernoe et al. |
| 7,713,238 B2 * | 5/2010 | Mernoe ............... 604/131 |
| 7,998,116 B2 * | 8/2011 | Mernoe ............... 604/131 |
| 8,226,608 B2 * | 7/2012 | Mernoe ............... 604/131 |
| 2001/0041869 A1 | 11/2001 | Causey, III et al. |
| 2001/0056262 A1 | 12/2001 | Cabiri |
| 2002/0004651 A1 | 1/2002 | Ljndggreen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073236 A1 | 3/2007 | Mernoe et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |

FOREIGN PATENT DOCUMENTS

| | | |
|---|---|---|
| DE | 102 36 669 | 2/2004 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| FR | 2 585 252 | 1/1987 |
| GB | 747 701 | 4/1956 |
| GB | 2 218 831 | 11/1989 |
| WO | WO 90/15928 | 12/1990 |
| WO | WO 97/21457 | 6/1997 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/057627 | 7/2002 |
| WO | WO 02/100469 | 12/2002 |
| WO | WO 03/103763 | 12/2003 |
| WO | WO 2004/056412 | 7/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/105792 | 10/2006 |
| WO | WO 2006/105793 | 10/2006 |
| WO | WO 2006/105794 | 10/2006 |

OTHER PUBLICATIONS

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

Medtronic News Release, "Medtronic Receives FDA Approval for World's First Insulin Pump with Real-time Continuous Glucose Monitoring," Apr. 13, 2006, 3 pages.

OmniPod Insulin Management System-Investor Relations—Press Release, Feb. 1, 2005, http://investors.insulet.com/phoenix.zhtml?c=209336&p=irol-newsArticle&ID=988708&highlight= 1 page.

OmniPod Quick Start Guide, 2007, 2 pages.

Patent Abstracts of Japan, vol. 1999, No. 04, and JP 11 010036 , Apr. 30, 1999 and Jan. 19, 1999, Toray Ind. Inc.

The Medtronic Diabetes Connection, 2006, 6 pages.

Xilas Temp Touch, "The latest in high-tech and convenient devices," DOCNews, vol. 2, No. 7, Jul. 1, 2005, http://docnews.diabetesjournals.org/cgi/content/full/2/7/13, 3 pages.

* cited by examiner

MEDICINE DISPENSING DEVICE

CROSS-REFERENCE TO RELATED APPLICATIONS

This application is a continuation of U.S. patent application Ser. No. 13/182,107 filed on Jul. 13, 2011 (now U.S. Pat. No. 8,226,608), which is a continuation of U.S. patent application Ser. No. 12/767,570 (now U.S. Pat. No. 7,998,116) filed on Apr. 26, 2010, which is a continuation of U.S. patent application Ser. No. 10/591,190 (now U.S. Pat. No. 7,713,238) filed on Aug. 31, 2006, which is a national stage application under 35 U.S.C. §371 that claims the benefit of PCT/DK2006/000195 (published as WO2006/105794) filed on Apr. 6, 2006, which claims priority to the following Denmark patent applications: serial no. PA 2005 00483 filed on Apr. 6, 2005, Ser. No. PA 2005 00542 filed on Apr. 14, 2005, and Ser. No. PA 2005 00817 filed on Jun. 3, 2005. The entire contents of these prior applications are incorporated herein by reference.

SUMMARY

The present invention relates to a method of dispensing liquid medicine comprising the steps of providing a wearable, disposable dispensing device comprising a syringe having a cylinder and a plunger displaceable in said syringe cylinder for pressing medicine out of said syringe cylinder and a drive mechanism connected to said plunger for displacing said plunger in said cylinder, and an electrical motor connected to a battery and to said drive mechanism for providing a rotary force to said driving mechanism for displacing said plunger, displacing said plunger a certain distance in connection with a cycle of said driving mechanism.

Methods of this type are known, wherein the electrical motor is controlled by a control means so as to carry out a certain number of revolutions for each cycle corresponding to the desired distance of displacement of the plunger.

In connection with such methods it is important that no more than the predetermined amount of medicine be dispensed per cycle as otherwise life threatening dosages may be dispensed.

When utilizing an electrical motor, a short circuit can entail that the motor does not stop after the predetermined number of revolutions or that the motor starts by itself.

Security means have been suggested to ensure that the predetermined dosage is not exceeded, for instance monitoring the amount of liquid dispensed per cycle or monitoring the displacement distance of the plunger or the amount of revolutions of the motor per cycle with interruption means being activated if the monitored elements exceed a certain value.

There exists a need for a simple and fail-safe method to avoid over-dosage of medicine. One main object of the invention is to meet this need.

According to the invention this object is achieved by the cycle comprising rotating said electrical motor in a first direction of rotation and subsequently rotating said electrical motor in the opposite direction of rotation.

Hereby, any short-circuit of the motor will not entail continued rotation of the motor in one direction with ensuing continued dispensing of medicine.

The invention furthermore relates to a wearable, disposable medicine dispensing device comprising:

a syringe having cylinder and a plunger displaceable in the syringe cylinder for pressing medicine out of said syringe cylinder,
a drive mechanism connected to said plunger for displacing said plunger in said cylinder, and
an electrical motor connected to a battery and to said drive mechanism for providing a rotary force to said driving mechanism for displacing said plunger, and
control means adapted for repeatedly reversing the direction of rotation of said electrical motor.

In a further aspect, the present invention relates to an actuator comprising:

a rotational motor.
one or more elongate, flexible elements such as a string, a filament, a strip, a ribbon and combinations thereof, said one or more elements being attached to said motor for rotation thereby and to a displaceable body, such that rotation of said motor twists said one or more elements and shortens the overall length thereof so that said displaceable body is displaced by the shortened element or elements.

Such an actuator according to the invention may be used in connection with medicine dispensing devices, but also in any application where a rotational force or movement is to be utilized to displace a body.

DESCRIPTION OF DRAWINGS

In the following the invention will be described more in detail in connection with two embodiments shown, solely by way of example, in the accompanying drawings, where.

DETAILED DESCRIPTION

Figure 1:
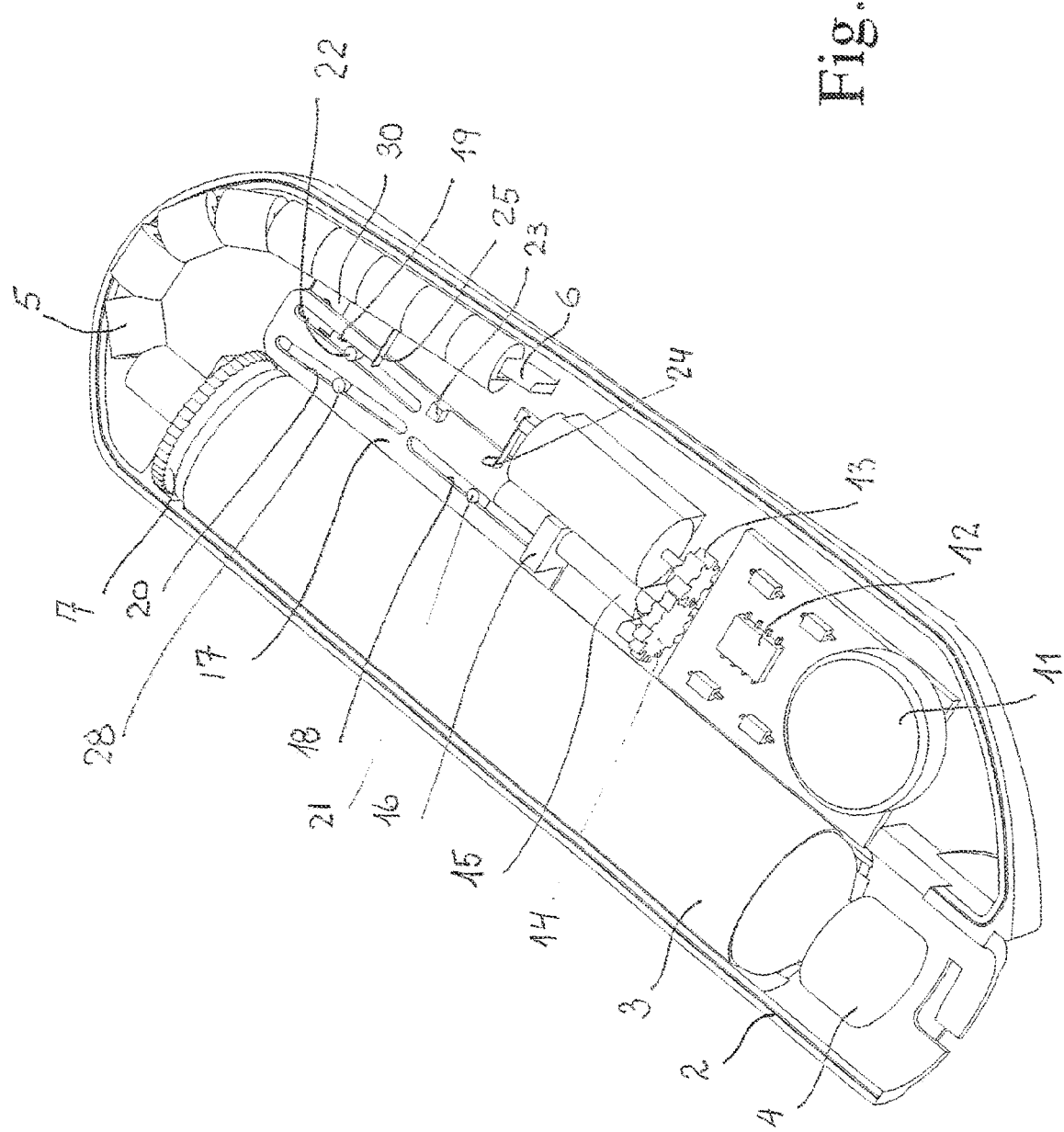
FIG. 1 shows a first embodiment of a device according to the invention seen in perspective and with the top part of the housing removed.
Figure 2:
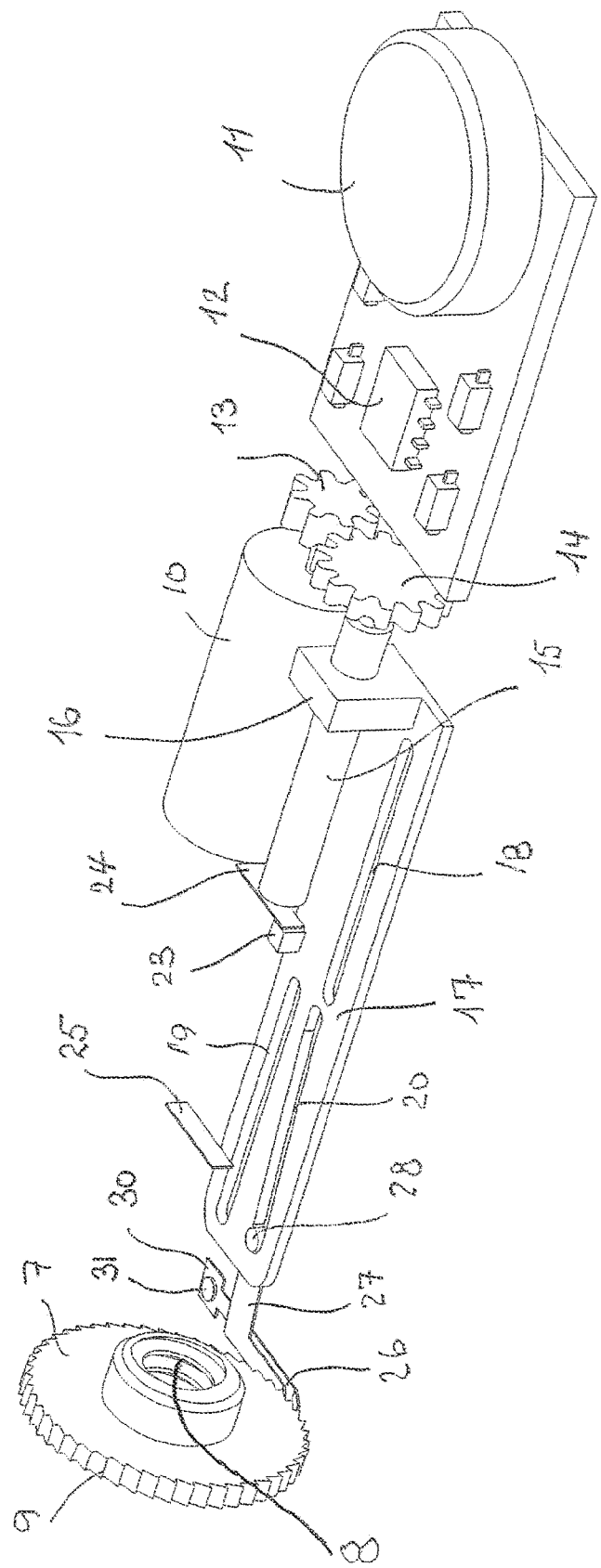
FIG. 2 shows a perspective view of the drive mechanism of the device according to the invention in FIG. 1.
Figure 3:
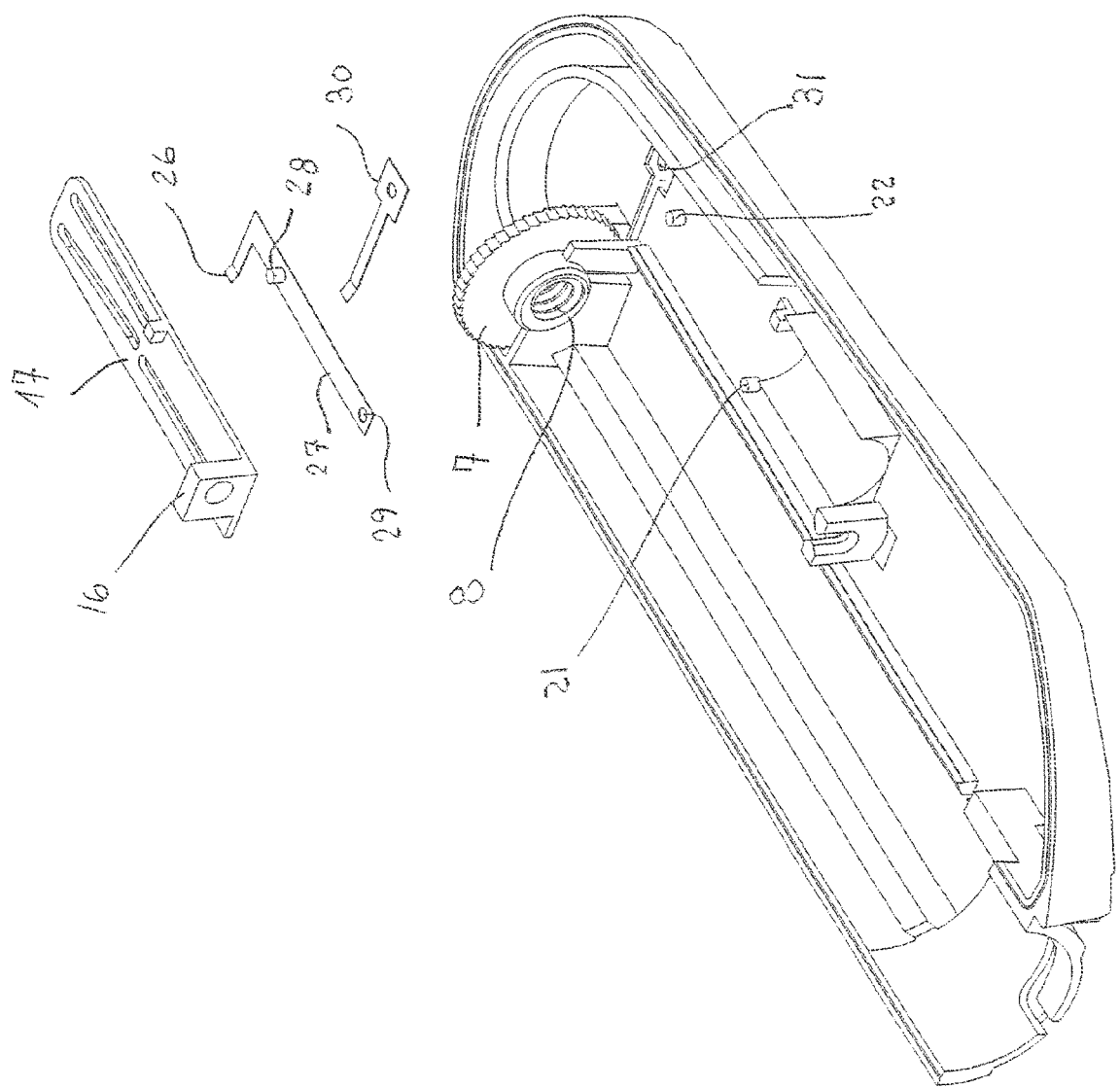
FIG. 3 is an exploded view of some of the drive mechanism elements of the device in FIG. 1, and FIGS. 4 and 5 are views corresponding to FIG. 2 with the drive mechanism in other positions.
Figure 4:
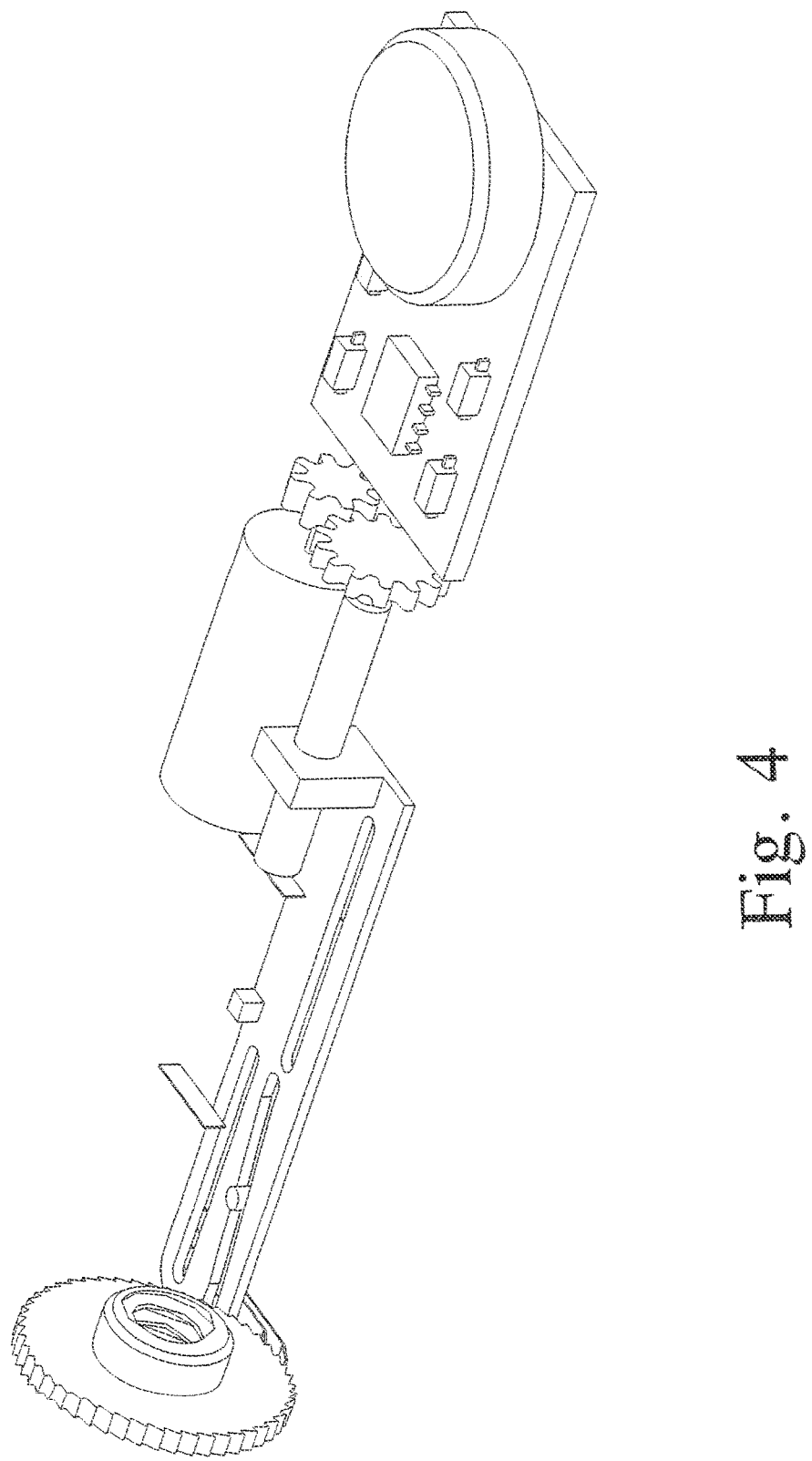
Figure 5:
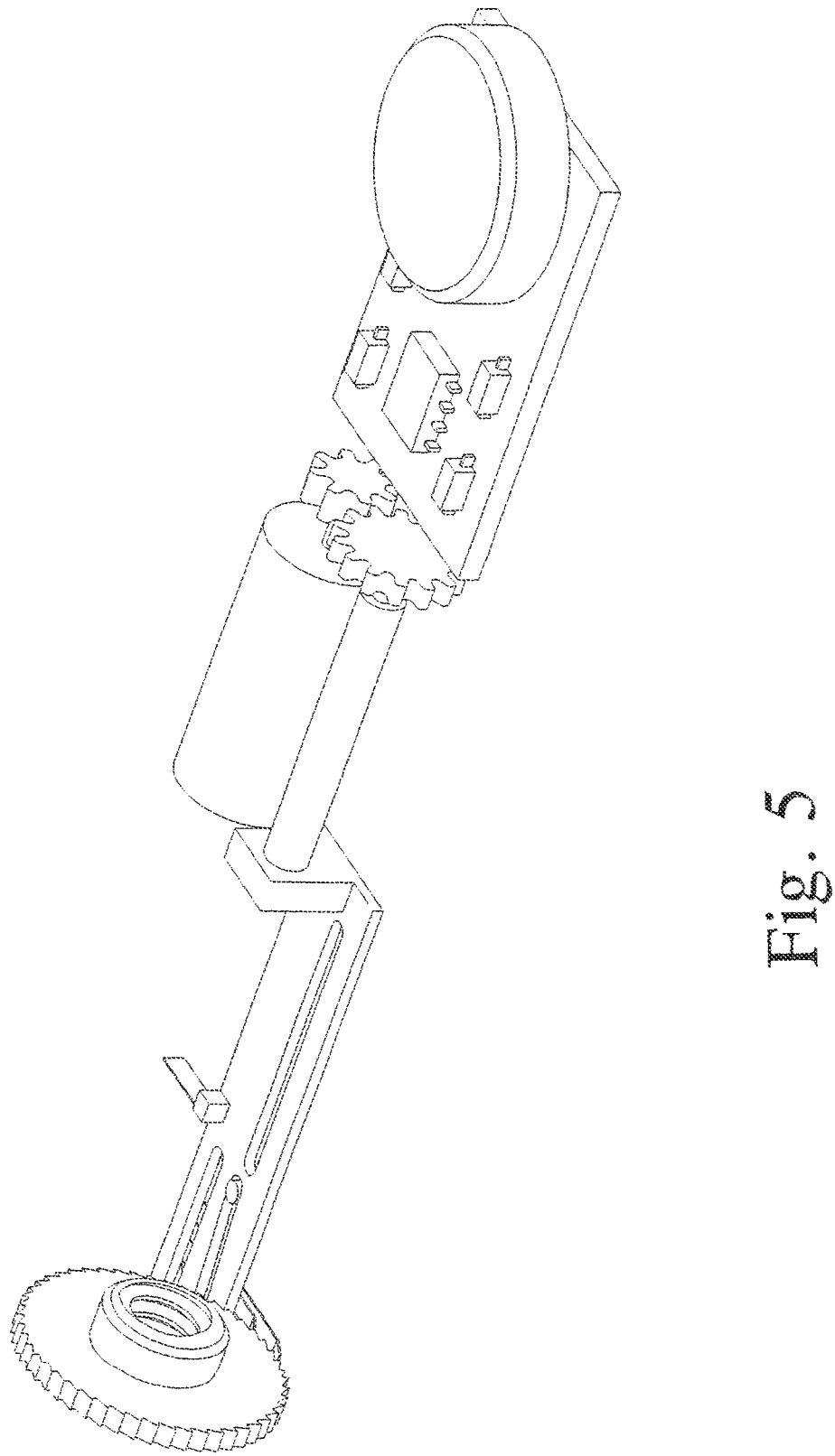
Figure 6:
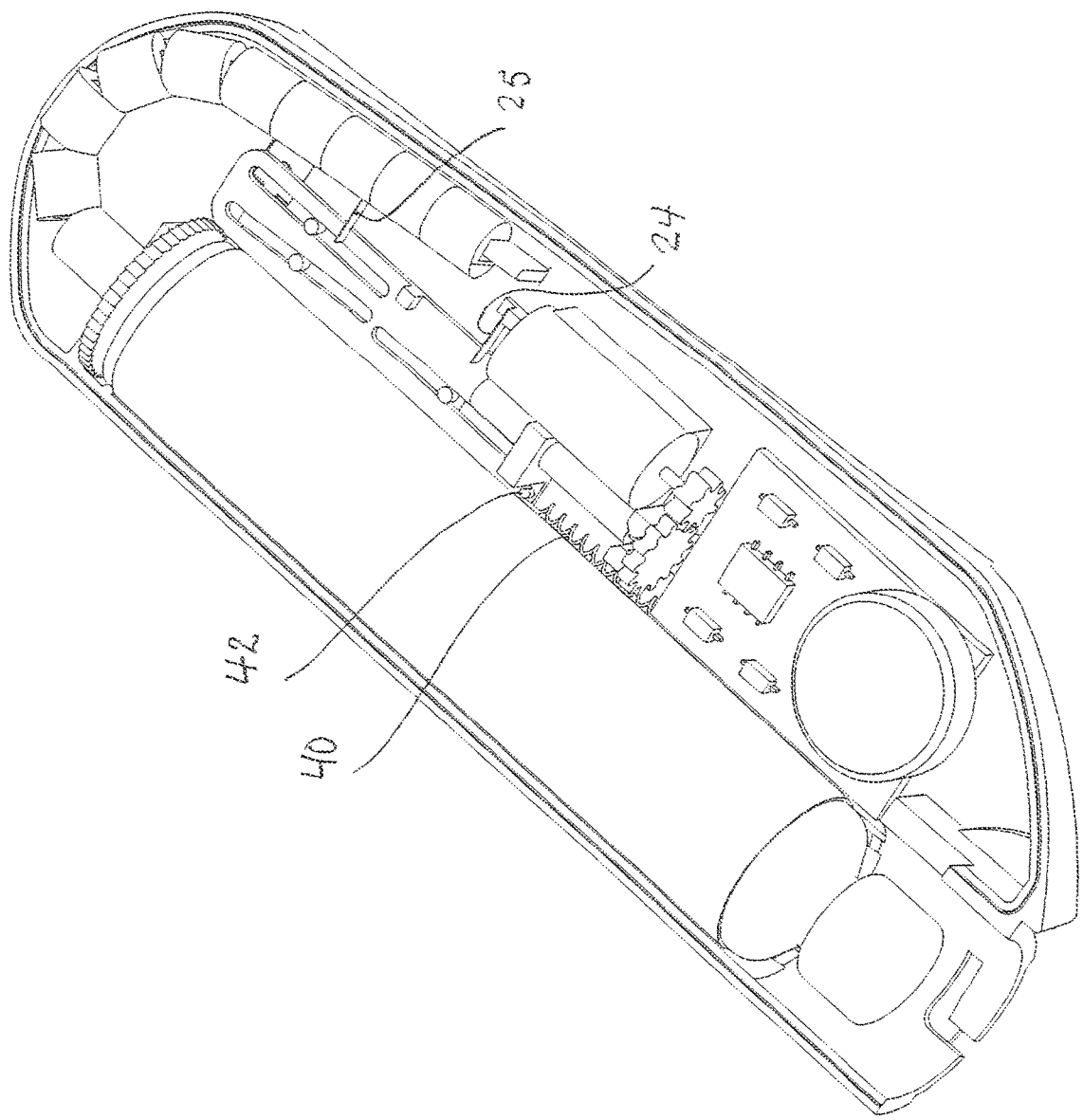
FIGS. 6-9 are views of a second embodiment of the device according to the invention corresponding to FIGS. 1, 2, 4 and 5, respectively.
Figure 7:
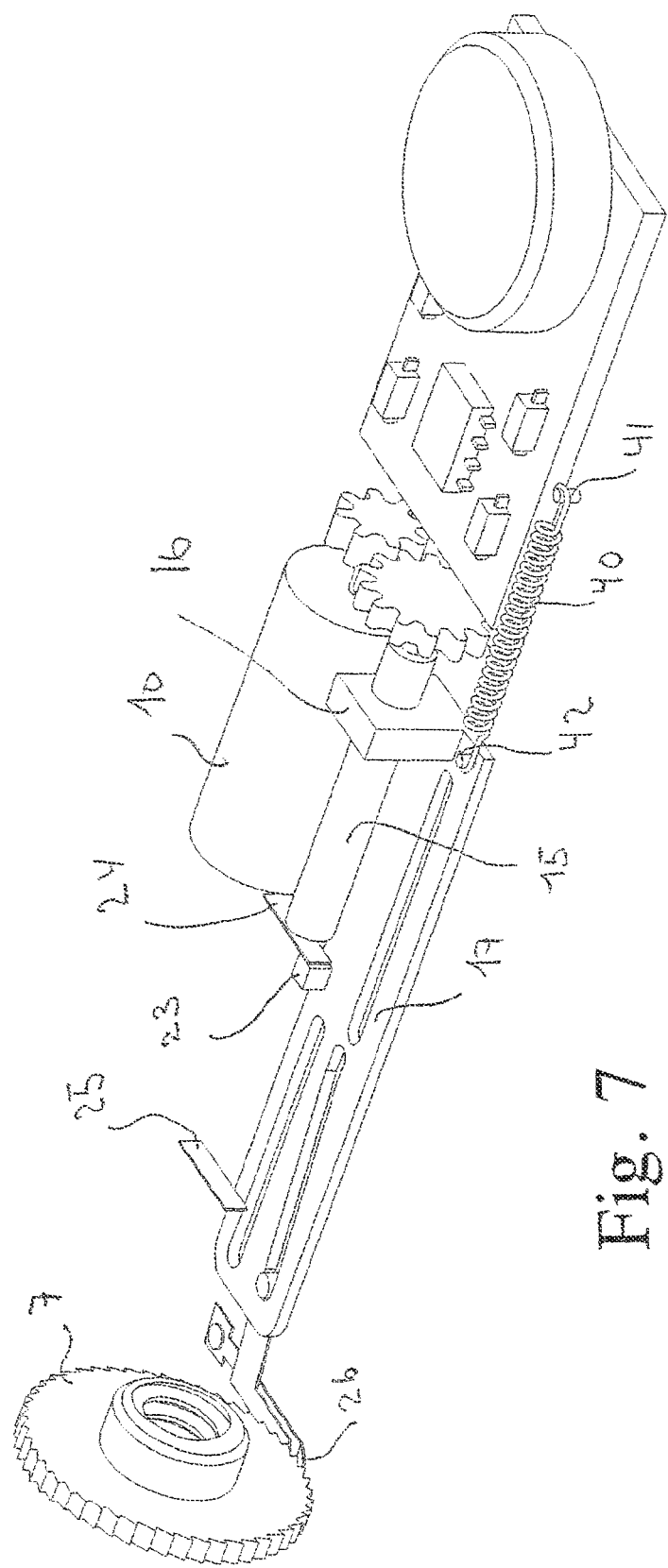
Figure 8:
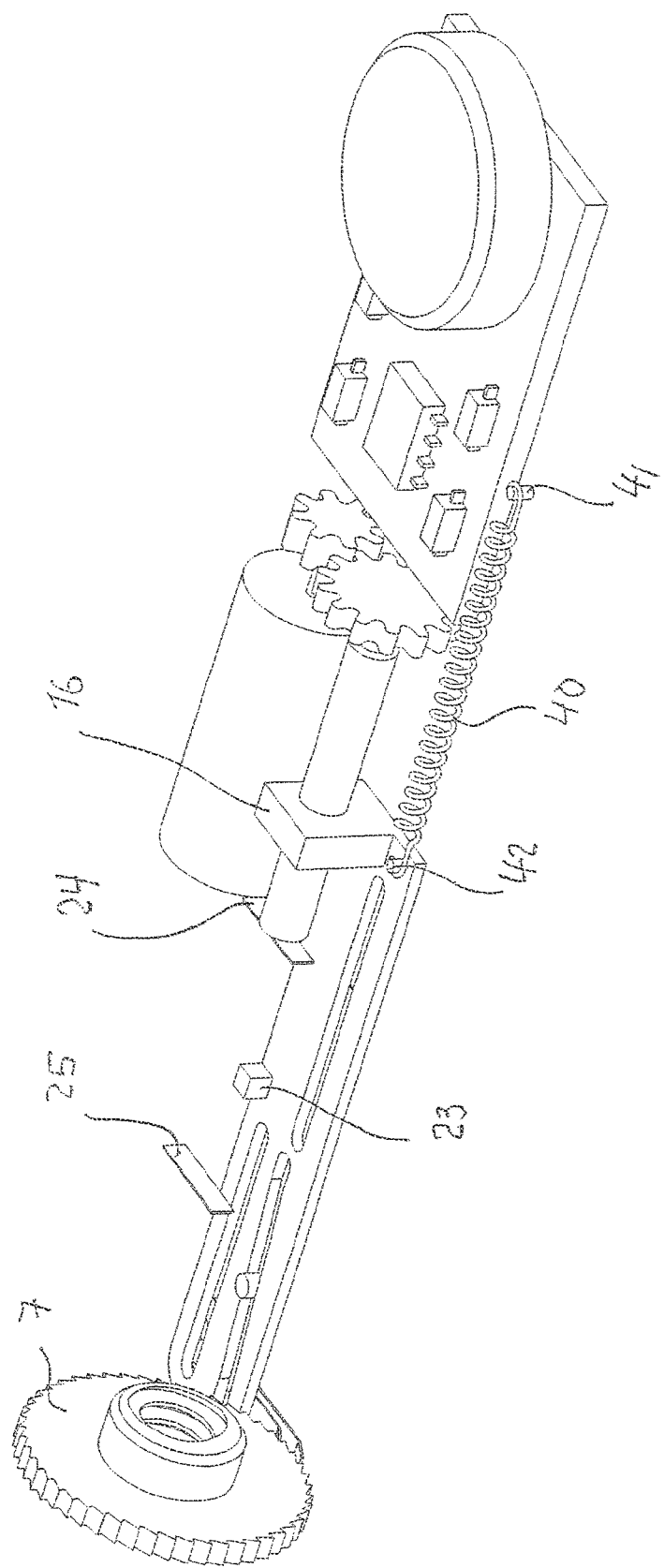
Figure 9:
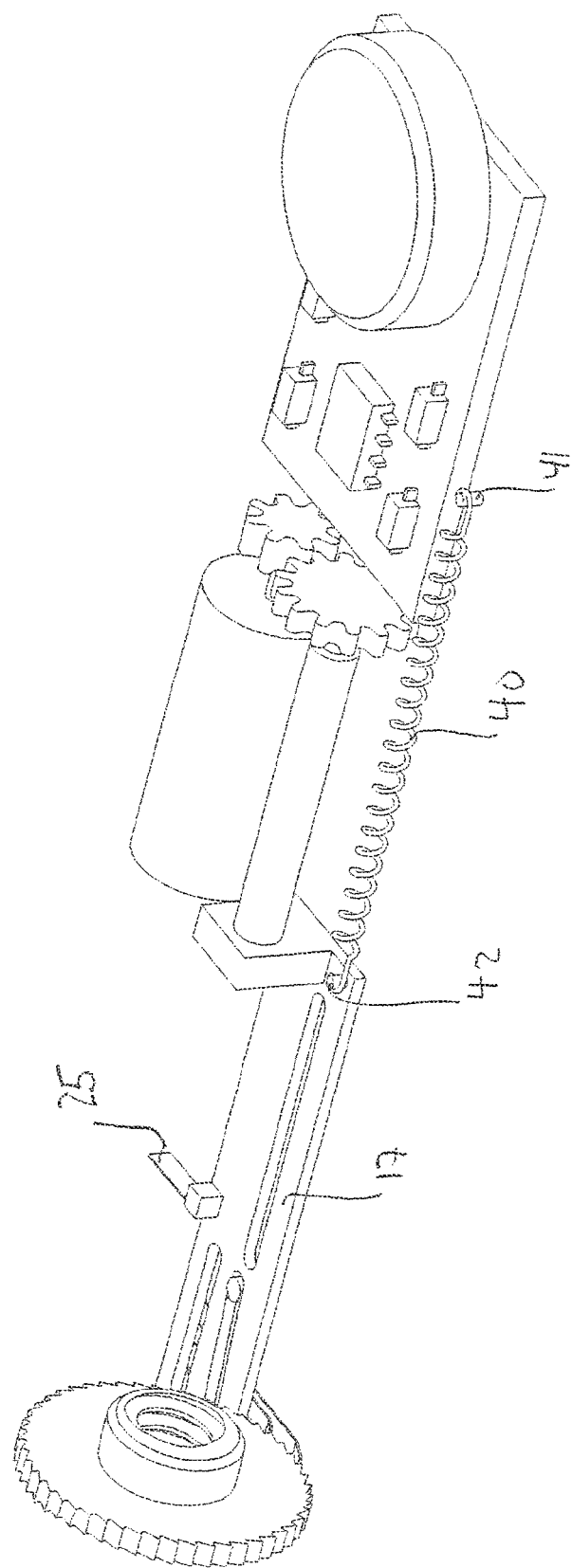
Figure 10:
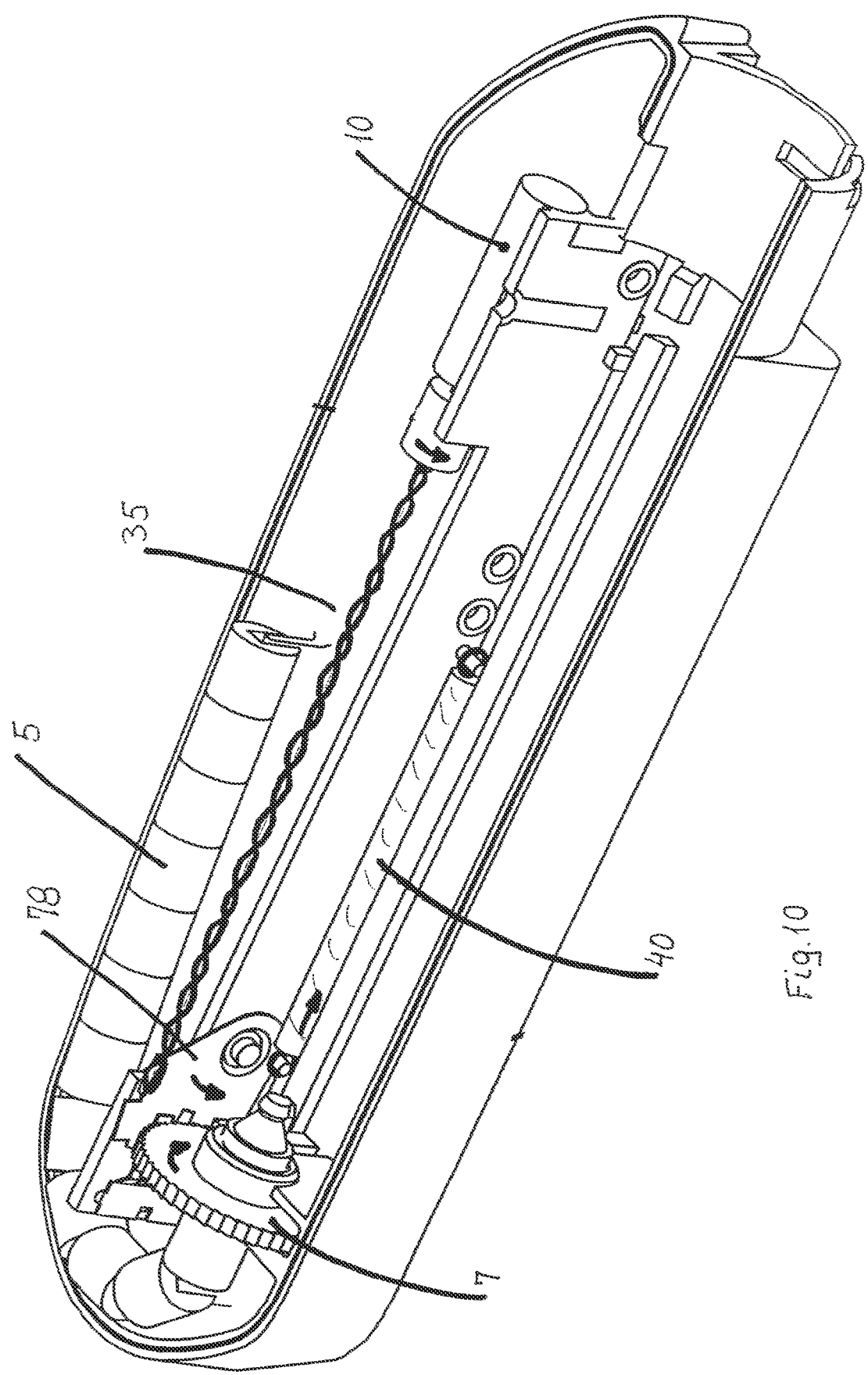
FIGS. 10-14 show a perspective view of a third embodiment of the device according to the invention in different sequential states during a first half cycle during rotation of the electrical motor in a first direction of rotation, FIGS. 15a, b and c are views of some of the drive mechanism elements of the device in FIGS. 10-14 in different states during the cycle.
Figure 11:
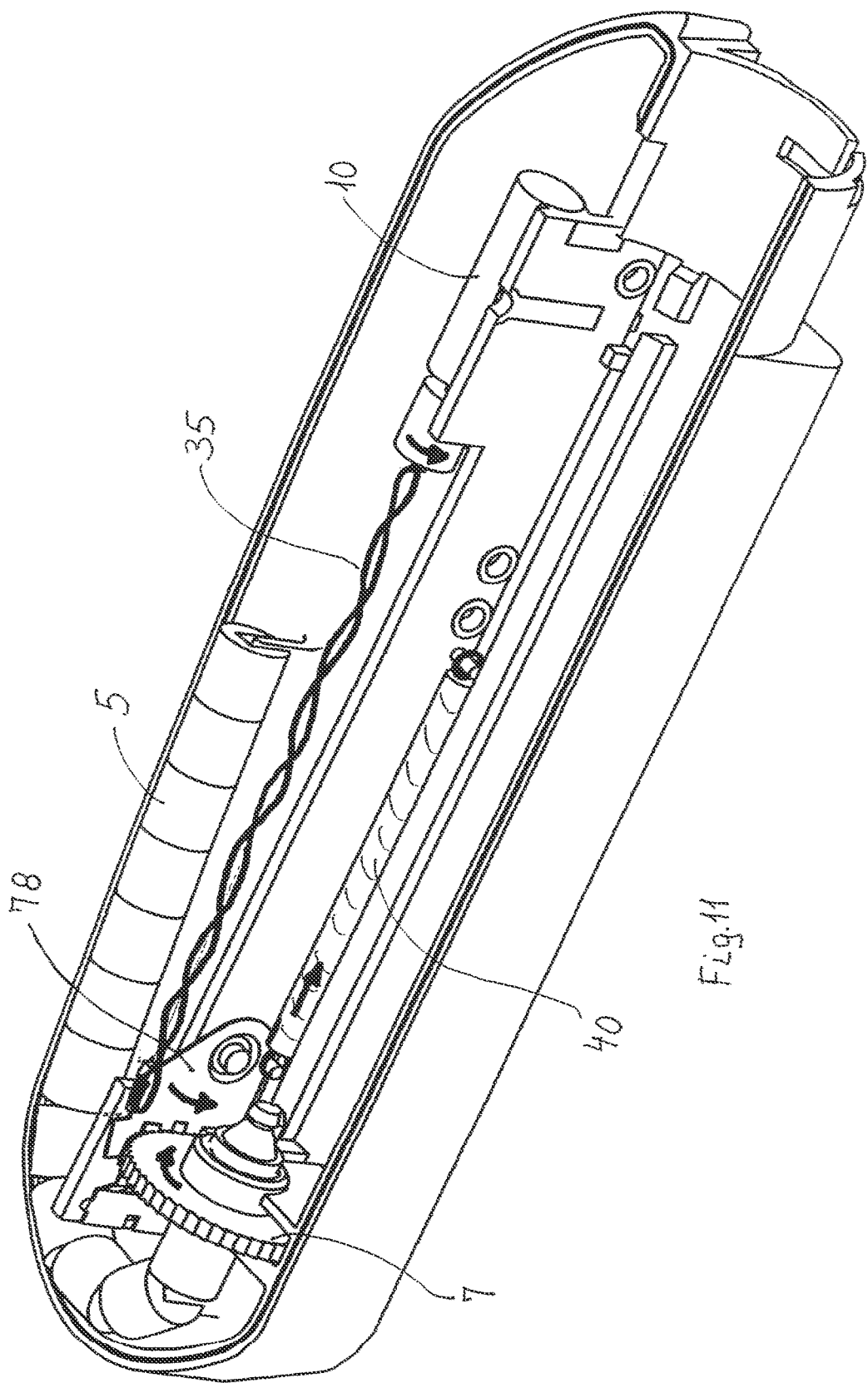
Figure 12:
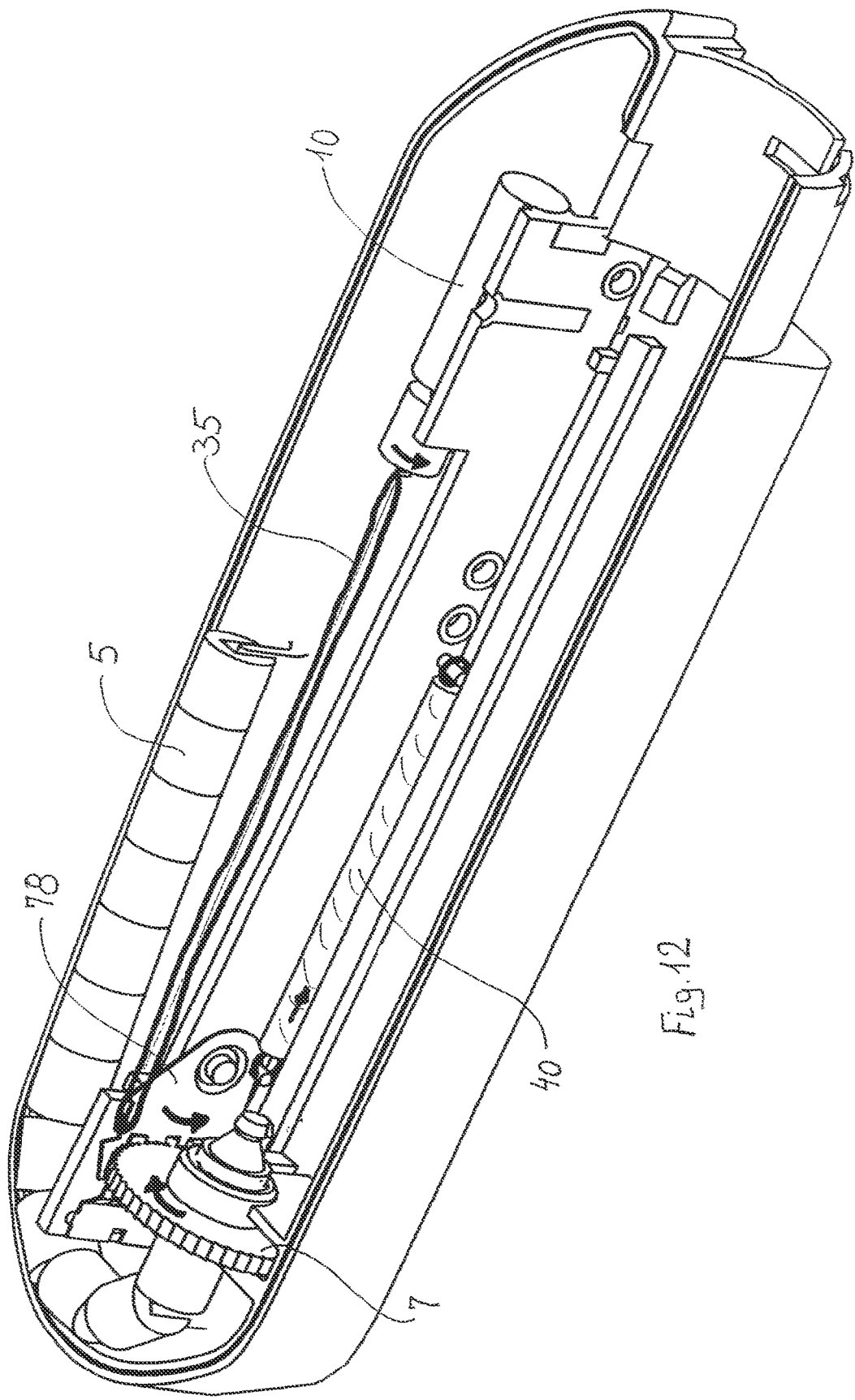
Figure 13:
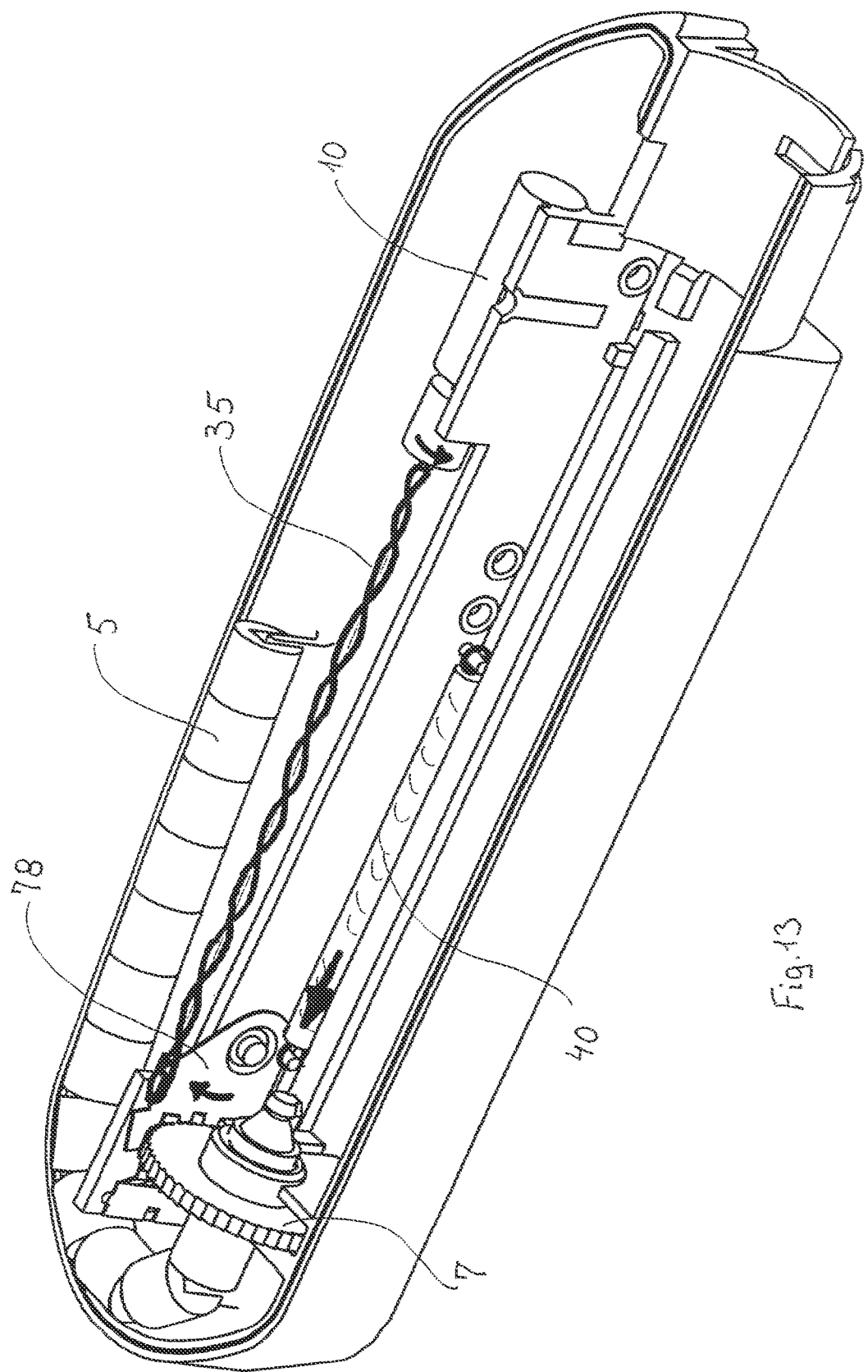
Figure 14:
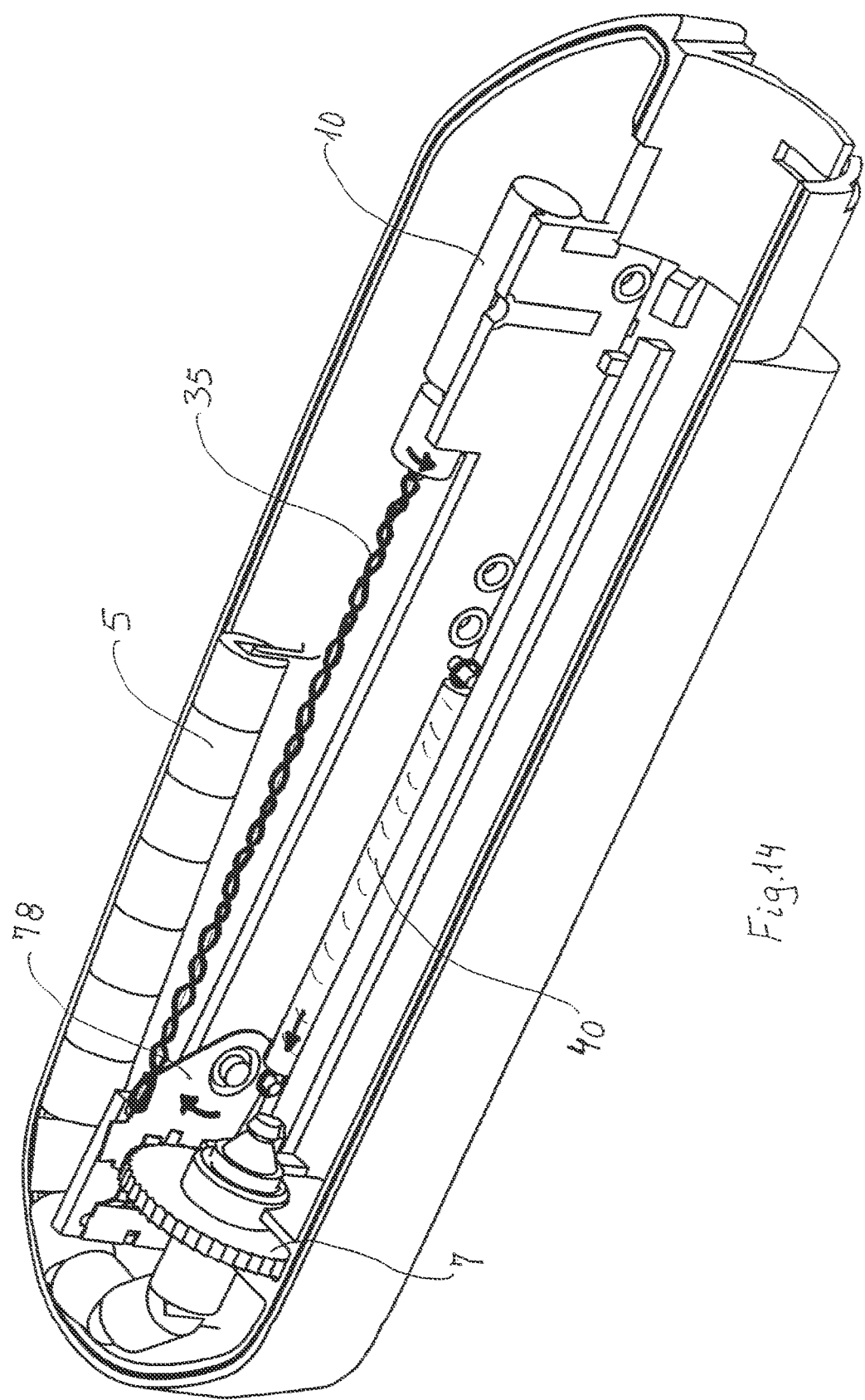
Figure 15:
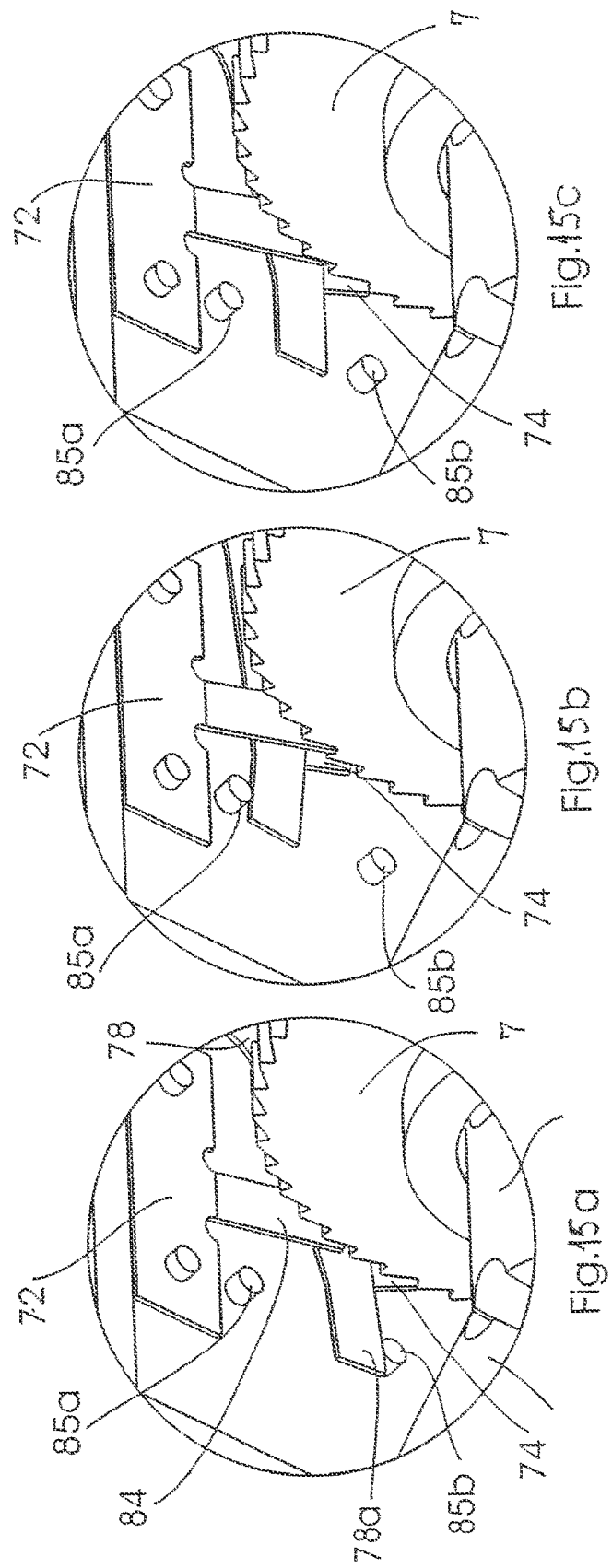

Referring now to FIGS. 1-5, a wearable disposable dispensing device for medicine referred to generally by the numeral 1 and of the type described in WO 2004/041330 and WO 2004/056412. the disclosure of which is hereby incorporated herein by reference, comprises a housing 2, where only the bottom half is shown for the sake of clarity, a cylindrical medicine container or carpule 3 having at one end a silicone body for receiving a catheter for dispensing medicine from the interior of the carpule to a human body and being open at the opposite end to receive a flexible piston rod 5 for displacing an internal not shown plunger or piston in the carpule 3 for forcing medicine out through a catheter needle assembly connected to the silicone body 4.

The flexible piston 5 is composed of segments hinged together and outwardly threaded guided by a rail 6 received in recesses in each of the segments of the rod 5. The not shown outward threads of the segments of the flexible piston rod 5 engage in a thread 8 of ratchet wheel 7 having teeth 9 along the periphery thereof. An electrical motor 10 electrically connected to a battery 11 and control means 12 is provided with a gear 13 meshing with a gear 14 attached to an outwardly threaded spindle or shaft 15 received in an inwardly threaded nut 16 attached a plate 17 provided with two slits 18 and 19, extending parallel to the axis of said spindle 15 and a third slit 20, extending at an angle to said axis. Two fixedly arranged pins 21 and 22 are received in the slits 18 and 19, respectively such that the pins serve as guides to the to and fro displacement of the plate 17 by means of the spindle 15 when the electrical motor 10 rotates first in one directional rotation and thereafter in the opposite directional rotation.

A protuberance 23 is arranged on the plate 17 to co-operate with two end stop contacts 24 and 25 electrically connected to the control means 12 for reversing the direction of rotation of the electrical motor when the protuberance 23 contacts one of the end stop contacts 24 or 25. A pawl 26 is attached to a pivotable elongated body 27 having a pin 28 for being received in the oblique slit 20 and a hole 29 for receiving the pin 21 such that the body 27 is pivotable around the pin 21. A ratchet 30 is fixedly attached to the housing 2 by means of a pin 31 and is located so as to engage the teeth 9 of the ratchet wheel 7. The pawl 26 is displaceable from a retracted position where it does not engage the teeth 9 of the ratchet wheel 7 and in an engaged position in which it engages the teeth of the ratchet wheel and rotates the ratchet wheel in a clockwise direction.

The displacement of the pawl 26 between the two positions indicated above takes place by the linear displacement of the plate 17. When the plate 17 is displaced in the direction from the end stop contact 24 to the end stop contact 25, the oblique slit 20 urges the pin 28 of the elongated body 27 in a direction 10 away from the carpule 3 such that the elongated body 27 pivots around the pin 21 in a clockwise direction, whereby the pawl 26 is moved in towards its retracted position relative to the ratchet wheel 7. When the protuberance 23 on the plate 17 contacts the end stop contact 25, the directional rotation of the motor 10 is reversed and the plate 17 is displaced in the direction from the end stop contact 25 towards the end stop contact 24, whereby the oblique slit 20 forces the pin 28 towards the carpule 3, whereby the elongated body 27 is forced to rotate in a counterclockwise direction whereby the pawl 26 is brought into contact with one of the teeth 9 of the ratchet wheel and rotates the ratchet wheel in a clockwise direction, while the ratchet rides over one of the other teeth 9 for locking the ratchet wheel against rotation in the counterclockwise direction.

Thus, during one cycle of rotation in one direction and the opposite direction of the electrical motor 10, the ratchet wheel 7 will be advanced by one tooth corresponding to one displacement of the pawl 26 from the retracted position thereof to the engaged position thereof.

Referring now to FIGS. 6-9, in this embodiment a coil spring 40 is attached to a pin 41 fixedly attached to the housing 2 and a pin 42 fixedly attached to the plate 17.

When the plate 17 is moved in the direction from end contact 24 towards the end contact 25, the spring 40 is in tension, and when the plate 17 moves back in a direction from the end stop contact 25 towards the end stop contact 24 after reversion of the direction of rotation of the motor 10, the spring 40 will be relaxed and exert a force in the same direction as the motor 10 on the plate 17 and thus reinforcing the force available to rotate the ratchet wheel 7.

Referring now to FIGS. 10-15, the electrical motor 10 is electrically connected to a battery and control means and the axle of the motor is connected to a pair of twisted strings 35 or a band or similar device, which reduces its length when twisted and increases its length when untwisted, said length variation being provided by the rotation of the motor, i.e. the device is connected to the rotating axle of the motor at one end and connected to a pivotable body 78 at the opposite end. The pivotable body is provided with an extension 78a comprising a pawl 74 arranged to engage the teeth 9 on the ratchet wheel 7, as indicated in FIGS. 15a. 15b. 15c. whereby the pivoting of the pivotable body 78 provides a rotation of the ratchet wheel 7. A second pawl mechanism 72, 84 is provided to prevent rotation of the ratchet wheel 7 in the opposite direction, again as shown in FIGS. 15a-15c.

The displacement of the pawl 74 between the two positions indicated in FIGS. 15a and 15b is provided by the reduction of the length of the twisted strings 35 by rotation of the motor and the displacement in the opposite direction is provided by the spring 40 during extension of the twisted strings 35 provided by rotation of the motor in the opposite direction, whereafter further rotation in this direction again reduces the length of the twisted strings 35, whereby a complete cycle of rotation in one direction of the motor provides a movement of the pivotable body from the position shown in FIG. 15a to the position shown in FIG. 15b and back to the position shown in FIG. 15a. this movement being provided by the twisted strings 35 being untwisted and twisted in the opposite direction during rotation of the motor in one direction. Thus, the rotation of the motor in one direction of rotation provides a full stroke for the pivotable body and thus the pawl mechanism moving the ratchet wheel one step forward and the following rotation of the motor in an opposite direction of rotation provides a further full stroke of the pivotable body and the pawl mechanism.

Thus, during one cycle of rotation in one direction and the opposite direction of the electrical motor 10, the ratchet wheel 7 will be advanced by two teeth corresponding to two displacements of the pawl 74. The pivotable body 78 comprises a protuberance 78a which co-operates with two end stop contacts 85a and 85b electrically connected to the control means for controlling the reversal of the direction of rotation of the electrical motor when the protuberance 78a contacts the end stop contact 85a. Due to the fact that the twisted strings 35 can only provide a pulling force on the pivotable body 78, a spring 40 is connected to the pivotable body to provide the movement in the direction shown by the arrow in FIG. 10.

In the embodiment shown in the figures spring 40 is a coil spring, however, other types of springs, such as a rod spring could be provided for this purpose.

Figure 16:
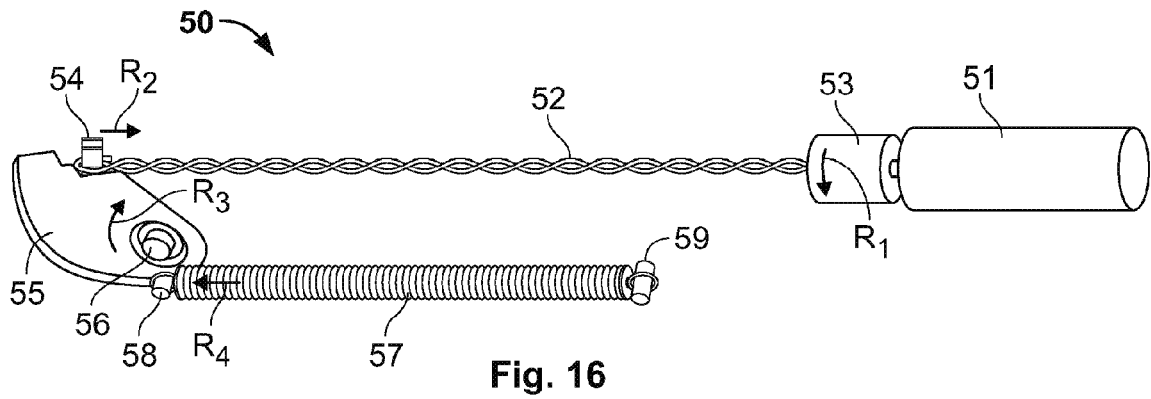
FIG. 16. is a schematic perspective view of a first embodiment of an actuator according to the invention, and FIGS. 17a-b very schematically show a second embodiment of an actuator according to the invention at two different phases of an actuation cycle.

Referring now to FIG. 16, an actuator according to the invention is referred to generally by the numeral 50 and is identical to the actuator shown in FIGS. 10-14. This actuator may be employed for any use requiring transformation of a rotation to a linear movement or a rotational force to a linear force.

A rotation motor 51 is attached to a pair of elongate, flexible elements such as strings or filaments 52 by means of a rotational body 53 that may or may not function as a fly wheel. The elements 52 are attached to a pin 54 on a pivotable plate. Rotation of the motor in the direction R1 will twist the strings 52 such that the length thereof is shortened until the pin 54 is displaced linearly in the direction R2 whereby the plate 55 is rotated around pivot 56 in the direction R3. A tension spring 57 is attached to plate 55 at pin 58 and to a not shown frame at pin 59.

Rotation of the plate 55 will expand the spring 57 in the direction R4 against the spring force thereof.

Rotation of the motor 51 in the direction opposite R1 will at first untwist the elements 52 whereby the length thereof becomes larger with the consequence that the spring 57 rotates the plate 55 in the direction opposite R3.

Further rotation of the motor 51 in the direction opposite R1 will twist the elements 52 again an eventually exert a force on said pin 54 in direction R2 again, the direction of rotation being subsequently reversed again and the cycle starts anew.

In case, a smaller interval is desired between each turn of the plate 55 in the direction R3, the motor 51 may reverse direction of rotation as soon the elements 52 have become untwisted to an extent that the spring 57 has pivoted the plate a certain distance in the direction opposite R3.

Figure 17A:
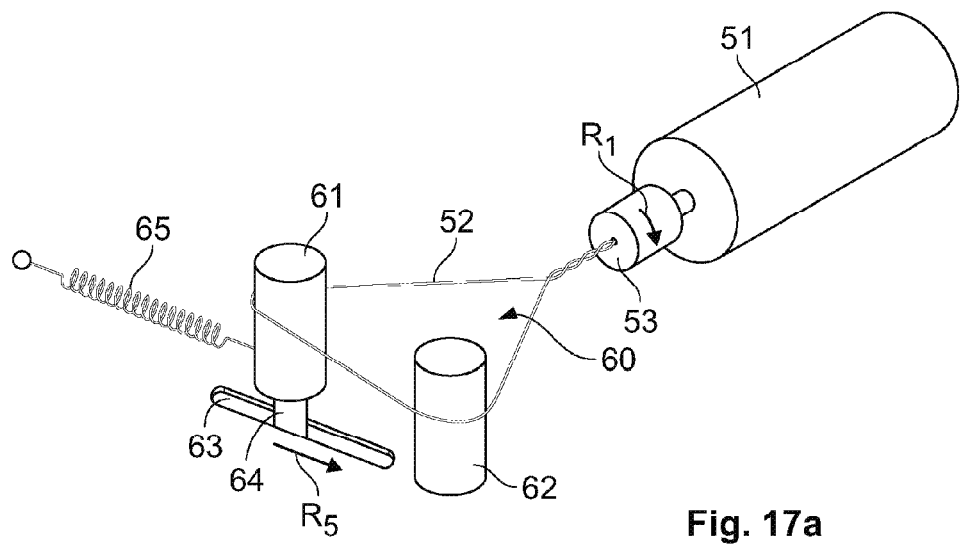
Figure 17B:
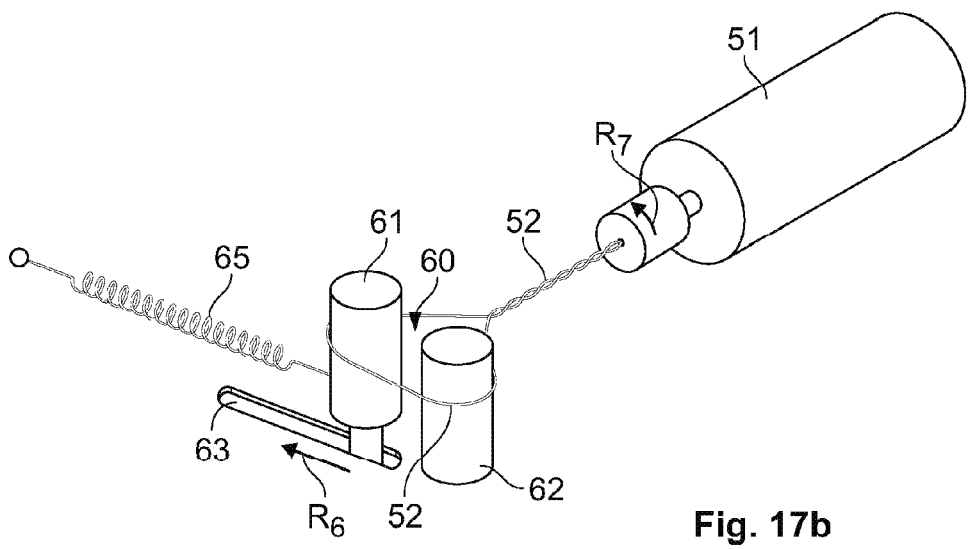

Reference is now made to FIGS. 17a-17b. where a motor 51 is attached to both opposed ends of an elongate, flexible element such as a string or filament 52 by means of a rotational body 53 that may or may not function as a fly wheel. The element 52 forms a loop 60 within which are located two bodies 61 and 62.

The body 61 is displaceable along a groove 63 in which a pin 64 of the body is slideably received. A spring 65 is attached to the displaceable body 61 such that displacement of said body 61 in the direction R5 takes place against the biasing force exerted by the spring 65.

The other body 62 is fixedly arranged such that when twisting of the element 52 by rotation of the motor 51 takes place the loop 60 is reduced in size as seen in FIG. 17b and the displaceable body 61 is forced towards the fixed body 62 along the groove 63 and against the spring force of the spring 65.

When the rotational direction of the motor is reversed so that it rotates in the direction R7, the element 52 will be untwisted, the loop 60 will enlarge and the spring 65 will displace the body in the direction R6.

Although the groove is shown extending substantially linearly, it may obviously be curved and extend at different angles to the axis of the motor.

The body 61 may be attached to a multitude of different driving or transmission mechanisms, for example the ratchet and pawl mechanisms shown in FIGS. 1-9.

A displaceable body should be taken to mean any body that can change position either by linear motion, curved motion, rotative motion, etc. and any combination thereof under the influence of a force applied to a point on or in said body.

Displacement should likewise be taken to mean any change in position resulting from linear motion, curved motion, rotative motion, etc. and any combination thereof.

What is claimed is:

1. A method of dispensing a medicine from a wearable medicine dispensing device, comprising:
rotating a battery-powered, reversible motor housed in wearable medicine dispensing device according to a motor rotation cycle that includes one or more full rotations of the reversible motor in a first rotational direction and one or more full rotations of the reversible motor in a second reverse rotational direction, wherein the rotation of the battery-powered, reversible motor according to said motor rotation cycle urges a drive mechanism housed in the wearable medicine dispensing device to advance a piston rod in a longitudinally forward increment toward a medicine in a reservoir arranged in the wearable medicine dispenser device; and
dispensing at least a portion of the medicine out of said reservoir arranged in the wearable medicine dispenser device in response to movement of the piston rod in said longitudinally forward increment.

2. The method of claim 1, further comprising repeating said rotating and said dispensing steps in a subsequent dispensation cycle for dispensing an additional portion of the medicine out of said reservoir.

3. The method of claim 1, wherein the wearable medicine dispenser device comprises a portable housing that defines a space for the reservoir containing the medicine.

4. The method of claim 3, wherein the portable housing of the wearable medicine dispenser device defines the space to slidably receive a medicine cartridge that serves as the reservoir, and wherein the step of dispensing the medicine comprises urging at least a portion of the medicine out of the medicine cartridge in response to movement of the piston rod in said longitudinally forward increment toward said medicine in the medicine cartridge.

5. The method of claim 3, wherein the drive mechanism is arranged in the portable housing and coupled to the piston rod so as to advance the piston rod in a series of the longitudinally forward increments.

6. The method of claim 5, wherein the drive mechanism comprises a pawl and a ratchet wheel, the pawl positioned to engage at least one of the teeth of the ratchet wheel, wherein the pawl reciprocates between a first position and a second position to incrementally rotate the ratchet wheel, wherein rotation of the ratchet wheel in a drive direction causes longitudinal advancement of the piston rod.

7. The method of claim 6, wherein the drive mechanism further comprises at least two gears coupled between the reversible motor and the pawl.

8. The method of claim 7, wherein the drive mechanism further comprises a rigid plate member coupled between the at least two gears and the pawl.

9. The method of claim 1, further comprising communicating signals from a control circuit device t to cause the reversible motor to repeatedly reverse the direction of rotation between the first rotational direction and the second reverse rotational direction.

10. The method of claim 9, wherein the wearable medicine dispensing device houses a sensor that communicates with the control circuit device to cause the rotation of the motor to be reversed from the first rotational direction to the second reverse rotational direction.

11. The method of claim 1, wherein the drive mechanism comprises a drive wheel to mate with a portion of the piston rod, wherein the drive wheel is locked from rotation in a direction opposite to a forward rotation drive direction of the drive wheel.

12. The method of claim 11, wherein the drive wheel comprises an internal thread configuration that engages with an outer thread configuration of the piston rod.

13. The method of claim 1, wherein the piston rod comprises a flexible piston rod having rod segments hinged together and outwardly threaded, wherein at least a portion of the flexible piston rod extends longitudinally in a curved configuration inside the wearable medicine dispensing device.

14. The method of claim 1, wherein the drive mechanism prevents over-dispensation of the medicine in the event of continuous rotation of the reversible motor in any of the first rotational direction and the second reverse rotational direction.

15. The method of claim 14, wherein the drive mechanism prevents over-dispensation of the medicine in the event of continuous rotation of the reversible motor so as to provide a fail-safe protection against over-dosage of medicine.

16. The method of claim 1, wherein the drive mechanism further comprises a linearly displaceable plate coupled to the reversible motor.

17. The method of claim 16, wherein one or more full rotations of the reversible motor causes the linearly displaceable plate to act upon a pawl of the drive mechanism.

18. The method of claim 1, wherein the wearable medicine dispensing device houses a battery in electrical connection with the reversible motor so as to provide power to rotate the reversible motor in a first direction and in a second reverse direction.

* * * * *